US009205426B2

(12) United States Patent
Koeda

(10) Patent No.: US 9,205,426 B2
(45) Date of Patent: Dec. 8, 2015

(54) BIOCHIP, REACTOR, AND REACTION METHOD

(75) Inventor: Hiroshi Koeda, Suwa (JP)

(73) Assignee: Seiko Epson Corporation (JP)

( * ) Notice: Subject to any disclaimer, the term of this patent is extended or adjusted under 35 U.S.C. 154(b) by 409 days.

(21) Appl. No.: 13/085,578

(22) Filed: Apr. 13, 2011

(65) Prior Publication Data

US 2011/0256590 A1 Oct. 20, 2011

(30) Foreign Application Priority Data

Apr. 14, 2010 (JP) ................................. 2010-092928

(51) Int. Cl.

| | |
|---|---|
| ***C12M 1/00*** | (2006.01) |
| ***C12M 1/34*** | (2006.01) |
| ***C12P 19/34*** | (2006.01) |
| ***C12Q 1/68*** | (2006.01) |
| ***G01N 15/06*** | (2006.01) |
| ***G01N 33/00*** | (2006.01) |
| ***G01N 33/48*** | (2006.01) |
| ***G01N 31/22*** | (2006.01) |
| ***G01N 33/52*** | (2006.01) |
| ***B01L 7/00*** | (2006.01) |
| *B01L 9/00* | (2006.01) |

(52) U.S. Cl.

CPC .. *B01L 7/525* (2013.01); *B01L 9/00* (2013.01); *B01L 2200/026* (2013.01); *B01L 2200/0642* (2013.01); *B01L 2300/0819* (2013.01); *B01L 2400/0481* (2013.01); *B01L 2400/0487* (2013.01); *B01L 2400/0633* (2013.01)

(58) Field of Classification Search

USPC ........... 435/6.1, 91.2, 283.1, 287.1; 422/68.1, 422/430

See application file for complete search history.

(56) References Cited

U.S. PATENT DOCUMENTS

| | | | | |
|---|---|---|---|---|
| 4,959,217 | A * | 9/1990 | Sanders et al. ................ | 424/473 |
| 7,101,354 | B2 * | 9/2006 | Thorne et al. ................. | 604/191 |
| 2008/0248586 | A1 * | 10/2008 | Tajima .......................... | 436/164 |
| 2009/0062740 | A1 * | 3/2009 | Thorne, Jr. .................... | 604/191 |

FOREIGN PATENT DOCUMENTS

| | | |
|---|---|---|
| JP | 2009-136250 | 6/2009 |
| JP | 2011-095164 A | 5/2011 |

* cited by examiner

*Primary Examiner* — Narayan Bhat

(74) *Attorney, Agent, or Firm* — Harness, Dickey & Pierce, P.L.C.

(57) ABSTRACT

A biochip includes: a chamber that has a longitudinal direction; a holding unit that holds a liquid sample within a predetermined area of the chamber provided along the longitudinal direction, and releases the liquid sample from the predetermined area to an area inside the chamber by using a predetermined pressing force; and a pressed member that applies the predetermined pressing force to the liquid sample.

8 Claims, 14 Drawing Sheets

BIOCHIP, REACTOR, AND REACTION METHOD

CROSS-REFERENCE

This application claims priority to Japanese Patent Application No. 2010-092928, filed Apr. 14, 2010, the entirety of which is hereby incorporated by reference.

BACKGROUND

1. Technical Field

The present invention relates to a biochip, a reactor, and a reaction method.

2. Related Art

Currently, with the recent reveal of the presence of genes concerned with various diseases, medical treatment utilizing genes such as genetic diagnosis and genetic treatment has been attracting attention. Moreover, a number of techniques utilizing genes have been developed in the fields of agriculture and stock-breeding for judgment and improvement of species. Thus, technologies associated with genes have been expanding in various fields these days. In utilizing genes, nucleic acid amplification technology is widely used at present. For example, PCR (polymerase chain reaction) is a typical known method as the nucleic acid amplification technology. Today, PCR is an essential technique for clarifying information on living substances.

According to tests using PCR, a method which causes reaction by using a sample reaction container called a tube or a chip (biochip) is generally employed. However, several problems arise from the method generally used, including a large quantity of necessary reagents or the like, complication of a device used for producing a necessary thermal cycle, and a long period for reaction. Therefore, such a biochip or a reactor which uses only a small amount of reagents or samples and performs PCR with high accuracy in a short period has been demanded.

For providing this type of biochip or reactor, JP-A-2009-136250 proposes a biochip and a reactor which produce a thermal cycle for reaction by reciprocating a liquid sample (liquid including a sample) contained as droplets in a tube filled with liquid (such as mineral oil) not miscible with the liquid sample and having a smaller specific gravity than that of the liquid sample.

According to this technology, however, a step for maintaining the liquid sample at a predetermined temperature for a predetermined period is required in many cases prior to start of PCR.

For example, in case of PCR performing hot start by using Taq polymerase, a maintenance period at 95° C. for about 5 minutes is required. For a test of an RNA virus such as an influenza virus, PCR is generally executed after reverse transcription from RNA to cDNA. In this case, a maintenance period at 45° C. for about 30 minutes is required, for example.

For providing the necessary maintenance temperature and maintenance period as above for the reactor disclosed in JP-A-2009-136250, a method which includes a step of maintaining the liquid sample at the predetermined temperature for the predetermined period by using another device, or a method which maintains the liquid sample at the predetermined temperature for the predetermined period while stopping the rotation of a holder holding a biochip is adopted, for example.

According to the former method, however, the labor of detaching the biochip from one device and attaching the biochip to the other device is required. In case of the latter method, the advantage that a plurality of biochips prepared at different times can be successively processed is not provided.

SUMMARY

An advantage of some aspects of the invention is to provide a biochip, a reactor, and a reaction method capable of performing a series of tests using PCR rapidly and efficiently.

(1) A biochip according to this aspect of the invention includes: a chamber which has a longitudinal direction; a holding unit which holds a liquid sample within a predetermined area of the chamber provided along the longitudinal direction, and releases the liquid sample from the predetermined area to an area inside the chamber by using a predetermined pressing force; and a pressed member which applies the predetermined pressing force to the liquid sample.

According to this aspect of the invention, the holding unit which holds the liquid sample within the predetermined area of the chamber provided along the longitudinal direction and releases the liquid sample from the predetermined area to an area inside the chamber by using the predetermined pressing force is provided. In this case, the condition of retaining the liquid sample within the predetermined area and the condition of allowing the liquid sample to shift to the outside of the predetermined area can be switched by using the predetermined pressing force. Accordingly, the biochip can perform a series of tests using PCR rapidly and efficiently by using a thermal cycler which reciprocates a liquid sample within liquid.

(2) The biochip according to the first aspect of the invention may be so constructed as to satisfy the following points: the chamber includes a first area corresponding to the predetermined area, and a second area elongated in the longitudinal direction; and the holding unit shifts the liquid sample from the first area to the second area by using the predetermined pressing force.

The biochip having this structure shifts the liquid sample to the second area elongated in the longitudinal direction by using the predetermined pressing force. Thus, the biochip can execute a series of tests using PCR rapidly and efficiently by using a thermal cycler which reciprocates a liquid sample within liquid.

(3) The biochip of the first aspect of the invention may be constructed such that the holding unit reduces the cross-sectional area of the chamber on the plane perpendicular to the longitudinal direction to an area smaller than the cross-sectional area of the predetermined area of the chamber on the plane perpendicular to the longitudinal direction.

This biochip has simplified structure and can execute a series of tests using PCR rapidly and efficiently by using a thermal cycler which reciprocates a liquid sample within liquid.

(4) The biochip of first aspect of the invention may be constructed such that the holding unit has a valve.

This biochip has simplified structure and can execute a series of tests using PCR rapidly and efficiently by using a thermal cycler which reciprocates a liquid sample within liquid.

(5) The biochip of the first aspect of the invention may further include: a first movable stopper which seals one end of the chamber in the longitudinal direction positioned near the predetermined area; and a second movable stopper which seals the other end of the chamber in the longitudinal direction. In this case, the pressed member corresponds to the first movable stopper.

According to this structure, the predetermined pressing force can be applied with the volume of the chamber kept substantially constant.

(6) The biochip of the first aspect of the invention may be so constructed as to satisfy the following points: the pressed member applies the predetermined pressing force to the liquid sample via the holding unit; and the holding unit releases the liquid sample and switches between the liquid sample contained within the predetermined area and oil charged into the chamber.

According to this structure, variations in the volume of the chamber produced when the predetermined pressing force is applied can be reduced.

(7) A reactor according to this aspect of the invention includes: a holder holding a biochip which includes a chamber having a longitudinal direction, a holding unit holding a liquid sample within a predetermined area of the chamber provided along the longitudinal direction and releasing the liquid sample from the predetermined area to an area inside the chamber by using a predetermined pressing force, and a pressed member which applies the predetermined pressing force to the liquid sample; a driving unit which rotates the holder around a rotation axis having a horizontal component; and a first heat block disposed within a first distance range from the rotational axis in such a condition that the temperature distribution of the first heat block becomes axis-symmetric with respect to the rotation axis and controlled to have a first temperature, and a second heat block disposed within a second distance range from the rotational axis as a range different from the first distance range in such a condition that the temperature distribution of the second heat block becomes axis-symmetric with respect to the rotation axis and controlled to have a second temperature different from the first temperature, under the condition in which the biochip is held in the holder. The holder is so constructed that the distance between the rotation axis and one end of the chamber in the longitudinal direction is different from the distance between the rotation axis and the other end of the chamber, and that at least a part of the predetermined area lies either within the first distance range from the rotation axis or within the second distance range from the rotation axis, under the condition in which the biochip is held in the holder.

According to this aspect of the invention, at least a part of the predetermined area lies either within the first distance range from the rotation axis or within the second distance range from the rotation axis. Thus, the liquid sample can be maintained in a predetermined temperature state under the condition of retaining the liquid sample within the predetermined area, and can be brought into a predetermined temperature cycle under the condition of allowing the liquid sample to shift to an area other than the predetermined area. Accordingly, the reactor can perform a series of tests using PCR rapidly and efficiently.

(8) A reaction method according to this aspect of the invention includes: injecting a liquid sample into a predetermined area of a chamber of a biochip which includes the chamber having a longitudinal direction, a holding unit holding the liquid sample within the predetermined area of the chamber provided along the longitudinal direction and releasing the liquid sample from the predetermined area to an area inside the chamber by using a predetermined pressing force, and a pressed member applying the predetermined pressing force to the liquid sample; disposing the predetermined area in such a condition as to have a predetermined temperature with the liquid sample retained within the predetermined area by using the holding unit, and rotating the biochip around a rotation axis located in such a position that the distance between the rotation axis and one end of the chamber in the longitudinal direction is different from the distance between the rotation axis and the other end of the chamber and having a horizontal component; applying the predetermined pressing force to the liquid sample by using the pressed member to release the liquid sample from the predetermined area to an area within the chamber; and rotating the biochip around the rotation axis.

According to this aspect of the invention, the condition of retaining the liquid sample within the predetermined area and the condition of allowing the liquid sample to shift to the outside of the predetermined area can be switched by applying the predetermined pressing force to the liquid sample using the pressed member and releasing the liquid sample from the predetermined area to an area within the chamber. In this case, the liquid sample can be maintained in a predetermined temperature state under the condition of retaining the liquid sample within the predetermined area, and can be brought into a predetermined temperature cycle under the condition of allowing the liquid sample to shift to the outside of the predetermined area. Accordingly, the reaction method can perform a series of tests using PCR rapidly and efficiently.

BRIEF DESCRIPTION OF THE DRAWINGS

The invention will be described with reference to the accompanying drawings, wherein like numbers reference like elements.

DESCRIPTION OF EXEMPLARY EMBODIMENTS

Preferred embodiments and examples according to the invention are hereinafter described in detail with reference to the drawings. It should be stated that any unreasonable limitations based on the description of the embodiments and examples herein are not allowed to be imposed on the scope of the invention defined by the appended claims. As such, all the constructions and parts described herein are not necessarily the essential elements for the invention.

1. Biochip in First Embodiment

Figure 1A:
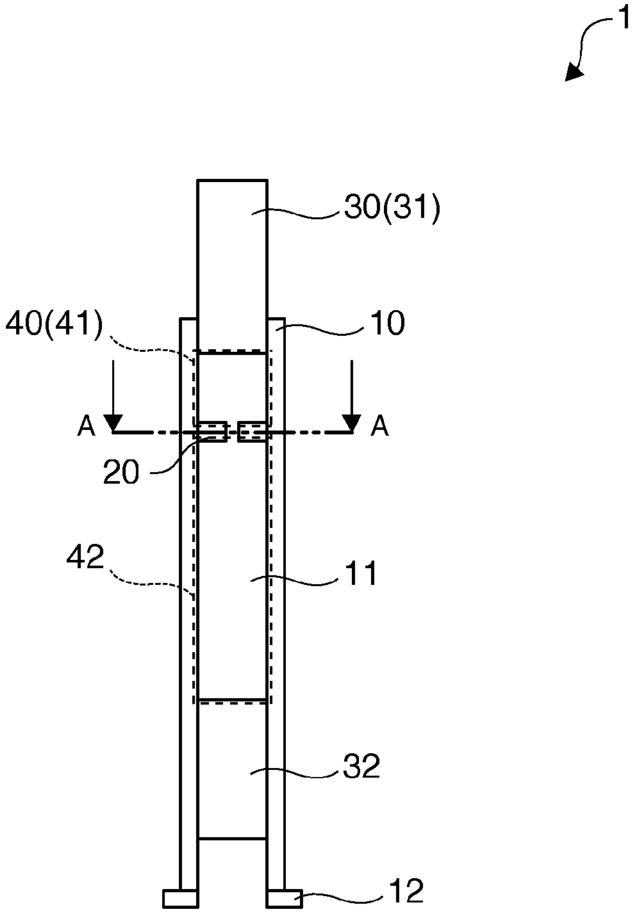
FIG. 1A schematically illustrates a cross-sectional structure of a biochip 1 according to a first embodiment.
Figure 1B:
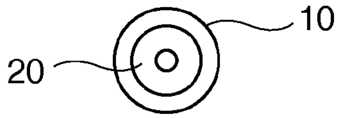
FIG. 1B schematically illustrates a cross section of the biochip 1 according to the first embodiment taken along a line A-A in FIG. 1A.

FIG. 1A schematically illustrates a cross-sectional structure of a biochip 1 according to a first embodiment. FIG. 1B schematically illustrates a cross section of the biochip 1 according to the first embodiment taken along a line A-A in FIG. 1A.

The biochip 1 in the first embodiment includes a chamber 11 having a longitudinal direction, a holding unit 20 which holds a liquid sample within a predetermined area 40 of the chamber 11 provided along the longitudinal direction and releases the liquid sample from the predetermined area 40 by using a predetermined pressing force, and a pressed member 30 which applies the predetermined pressing force to the liquid sample.

The external shape of the biochip 1 is arbitrarily determined. The size and shape of the biochip 1 are not specifically limited but may be selected according to the purpose of use, considering at least one of conditions including the quantity of charged liquid such as oil, the thermal conductivity, the shape of the chamber 11 formed inside, and the handling easiness of the biochip 1, for example.

The material of the biochip 1 is not specifically limited. For example, the biochip 1 may be made of an inorganic material (such as pyrex glass (pyrex: trademark)), an organic material (such as polycarbonate, polypropylene and other resins), or a composite material of these materials. When the biochip 1 is used as a reaction container (reaction chip) for a purpose accompanied with fluorometry such as PCR (polymerase chain reaction), it is preferable that the biochip 1 is made of material producing low self-fluorescence. Examples of the material producing low self-fluorescence involve polycarbonate and polypropylene. When the biochip 1 is used as a reaction container for PCR, it is preferable that the biochip 1 is made of material endurable for heat generated by PCR.

The biochip 1 may be mixed with black material such as carbon black, graphite, titanium black, aniline black, oxide of Ru, Mn, Ni, Cr, Fe, Co or Cu, and carbide of Si, Ti, Ta, Zr or Cr. When the black material is added to the material of the biochip 1, self-fluorescence from resin can be further reduced. When the biochip 1 is used for a purpose requiring observation of the inside of the chamber 11 from the outside of the biochip 1 (such as real time PCR), the biochip 1 may be made of transparent material as necessary. When the biochip 1 is used as a reaction chip for PCR, it is preferable that the biochip 1 is made of material which absorbs a smaller quantity of nucleic acid and protein and does not retard enzymatic reaction caused by polymerase or the like.

The biochip 1 shown in FIGS. 1A and 1B has the chamber 11 constituted by a part of a hollow portion of a body 10 as a substantially hollow and cylindrical component. As illustrated in FIG. 1A, a fringe 12 may be provided on the end portion of the body 10.

According to the example shown in FIG. 1A, the chamber 11 is formed in such a shape as to have the longitudinal direction corresponding to the direction of the center axis of the substantially hollow and cylindrical body 10 (vertical direction in FIG. 1A).

When the chamber 11 is long and narrow, a distance of separation between areas having different temperatures can be easily produced within the chamber 11 of the biochip 1 controlled in such a manner as to form the different temperature areas therein by using a thermal cycler of a type which reciprocates a liquid sample within liquid, for example. The thermal cycler which reciprocates the liquid sample within the liquid herein is a device which allows the liquid sample contained in the form of droplets in the reaction container filled with liquid not miscible with the liquid sample and having a smaller specific gravity than that of the liquid sample (such as mineral oil) to reciprocate between an area having a certain temperature and an area having a different temperature for producing a thermal cycle.

When the chamber 11 is long and narrow, the ratio of the surface area of the container to the volume of the container increases. Thus, when the chamber 11 is filled with liquid such as oil, the efficiency of heat conduction improves, for example. As a result, control over the temperature of the liquid becomes easier.

One of the functions of the chamber 11 is that the chamber 11 forms a reaction chamber for liquid when charged with the liquid. For example, the chamber 11 charged with PCR reaction liquid as a liquid sample and oil becomes a space where reaction of the PCR reaction liquid occurs. Particularly, when the chamber 11 is long and narrow, a thermal cycle can be easily produced for the PCR reaction liquid by shifting the PCR reaction liquid between different areas inside the chamber by the function of the thermal cycler of the type reciprocating the liquid sample within the liquid.

According to the biochip 1 shown in FIG. 1A, the chamber 11 includes a first area 41 forming a predetermined area 40, and a second area 42 elongated in the longitudinal direction of the chamber 11. Thus, in case of the biochip 1 shown in FIG. 1A, the second area 42 is provided as an area longer than the first area 41 in the longitudinal direction of the chamber 11. According to the example shown in FIG. 1A, the first area 41 and the second area 42 are separated from each other by the holding unit 20 provided on the inner surface of the body 10 (that is, inside the chamber 11).

The holding unit 20 holds the liquid sample within the predetermined area 40 of the chamber 11 provided along the longitudinal direction, and releases the liquid sample from the predetermined area 40 to an area within the chamber 11 by using a predetermined pressing force. According to the example of the biochip 1 shown in FIGS. 1A and 1B, the holding unit 20 is so structured as to shift the liquid sample from the first area 41 to the second area 42 by a predetermined pressing force.

More specifically, according to the example of the biochip 1 shown in FIGS. 1A and 1B, the holding unit 20 is constituted by a component which reduces the cross-sectional area of the chamber 11 on the plane perpendicular to the longitudinal direction of the chamber 11 to an area smaller than the cross-sectional area of the predetermined area 40 (that is, the first area 41) of the chamber 11 on the plane perpendicular to the longitudinal direction of the chamber 11. The surface of the holding unit 20 may have water repellency.

According to the example of the biochip 1 shown in FIGS. 1A and 1B, the holding unit 20 is a circular plate-shaped component having a circular opening at the center, and is supported with the circumference of the holding unit 20 closely contacting the inner surface of the body 10. The size of the opening is arbitrarily determined as long as the liquid sample can be retained within the predetermined area 40 (first area 41) before the predetermined pressing force is applied to the liquid sample, and can flow through the opening to reach the second area 42 when the predetermined pressing force is applied to the liquid sample. The shape of the opening is not limited to the circular shape but may be a polygonal shape, for example. The biochip 1 may have a plurality of the openings.

The pressed member 30 applies the predetermined pressing force to the liquid sample placed within the predetermined area 40. According to the example of the biochip 1 shown in FIGS. 1A and 1B, the biochip 1 includes a first movable stopper 31 for sealing one end of the chamber 11 in the longitudinal direction as an end closer to the predetermined area 40, and a second movable stopper 32 for sealing the other end of the chamber 11 in the longitudinal direction. In this example, the pressed member 30 is provided as the first movable stopper 31. The biochip 1 can apply the predetermined pressing force to the liquid sample placed within the predetermined area 40 (first area 41) by giving a force from the outside to at least either the first movable stopper 31 or the body 10 in such a manner as to reduce the distance between the first movable stopper 31 and the holding unit 20.

The first movable stopper 31 and the second movable stopper 32 are so structured as to prevent leakage of the liquid sample, the oil and the like charged into the chamber 11 to the outside of the chamber 11, and to be movable at least in a predetermined range within the chamber 11. In this structure, the biochip 1 can maintain the volume of the chamber 11 substantially constant by decreasing the distance between the first movable stopper 31 and the holding unit 20 and simultaneously increasing the distance between the second movable stopper 32 and the holding unit 20. Thus, the biochip 1 having the first movable stopper 31 and the second movable stopper 32 at both ends of the chamber 11 can apply the predetermined pressing force with the volume of the chamber 11 kept substantially constant.

According to the biochip 1 in the first embodiment thus constructed, the holding unit 20 which holds the liquid sample within the predetermined area 40 of the chamber 11 provided along the longitudinal direction and releases the liquid sample from the predetermined area 40 to an area within the chamber 11 by using the predetermined pressing force is provided. In this structure, the condition of retaining the liquid sample within the predetermined area 40 and the condition of allowing the liquid sample to shift to the outside of the predetermined area 40 can be switched by using the predetermined pressing force. Accordingly, the liquid sample can be placed in a predetermined temperature range under the condition of retaining the liquid sample within the predetermined area 40 regardless of the rotation of the thermal cycler of the type reciprocating the liquid sample within the liquid, and can be brought into a temperature cycle under the condition of allowing the liquid sample to shift to the outside of the predetermined area 40 according to the rotation of the thermal cycler of the type reciprocating the liquid sample within the liquid.

In this case, the labor for conveying a biochip from other device to the thermal cycler of the type reciprocating a liquid sample within liquid is eliminated. Moreover, a plurality of biochips prepared at different times can be successively processed by using a single thermal cycler. Thus, the biochip 1 can execute a series of tests using PCR rapidly and efficiently by using the thermal cycler of the above type.

Accordingly, the biochip 1 which shifts the liquid sample from the predetermined area 40 (first area 41) to the second area 42 elongated in the longitudinal direction by using the predetermined pressing force becomes a biochip capable of executing a series of tests using PCR rapidly and efficiently by using the thermal cycler of the type reciprocating a liquid sample within liquid.

The biochip 1 has the holding unit 20 which reduces the cross-sectional area of the chamber 11 on the plane perpendicular to the longitudinal direction of the chamber 11 to an area smaller than the cross-sectional area of the predetermined area 40 (that is, first area 41) of the chamber 11 on the plane perpendicular to the longitudinal direction of the chamber 11. Thus, the biochip 1 becomes a biochip having a simple structure and capable of executing a series of tests using PCR rapidly and efficiently by using the thermal cycler of the type reciprocating a liquid sample within liquid.

Oil not miscible with the liquid sample may be charged into the chamber 11 of the biochip 1. In this case, PCR can be easily carried out by using the thermal cycler of the type reciprocating a liquid sample within liquid.

The inside of the chamber 11 of the biochip 1 may be coated with at least either primer for amplifying the target nucleic acid or a fluorescent probe for detecting PCR products. In this case, mixture of the liquid sample and at least either the primer for amplifying the target nucleic acid or the fluorescent probe for detecting PCR products can be achieved through divided injection of the liquid sample into the biochip. By this method, execution of PCR can be further facilitated.

2. Biochip in Second Embodiment

Figure 2A:
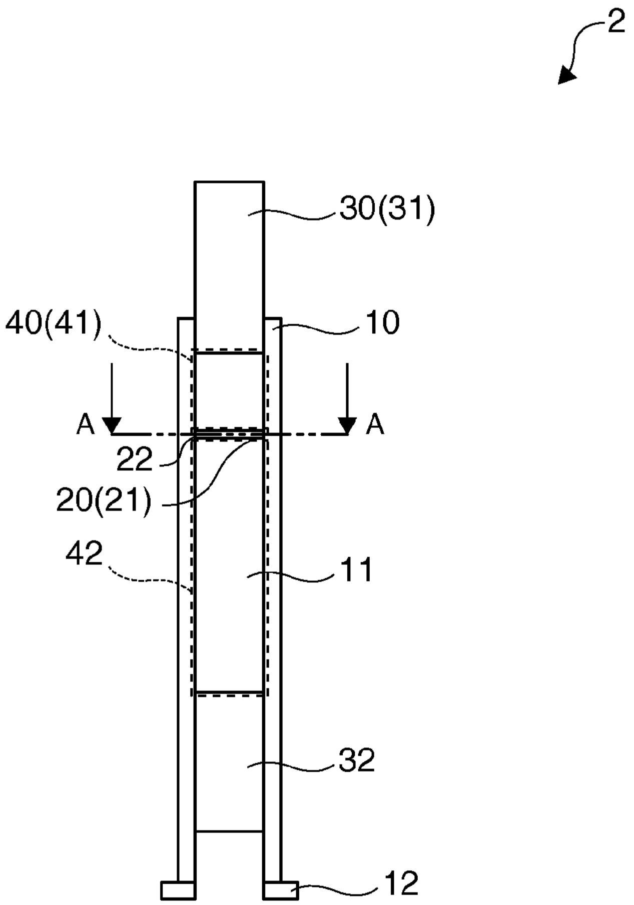
FIG. 2A schematically illustrates a cross-sectional structure of a biochip 2 according to a second embodiment.
Figure 2B:
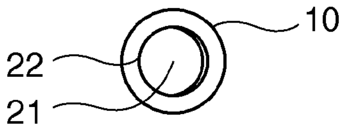
FIG. 2B schematically illustrates a cross section of the biochip 2 according to the second embodiment taken along a line A-A in FIG. 2A.

FIG. 2A schematically illustrates a cross-sectional structure of a biochip 2 according to a second embodiment. FIG. 2B schematically illustrates a cross section of the biochip 2 in the second embodiment taken along a line A-A in FIG. 2A.

The biochip 2 in the second embodiment has structure similar to that of the biochip 1 in the first embodiment except for the construction of the holding unit 20. Thus, similar reference numbers are given to the parts similar to the corresponding parts of the biochip 1 in the first embodiment, and the structure of the holding unit 20 of the biochip 2 is particularly touched upon in the following description.

The holding unit 20 of the biochip 2 according to the second embodiment has a valve 21. According to the example shown in FIGS. 2A and 2B, the holding unit 20 has the valve 21 supported by connection between a support portion 22 and a part of the inner surface of the body 10. The valve 21 is so constructed as to open and close a part of the chamber 11 with the fulcrum located at the support portion 22. Thus, in case of the example shown in FIGS. 2A and 2B, the valve 21 functions as a partitioning valve.

The degree of elasticity of the valve 21 may be arbitrarily determined as long as the valve 21 can retain the liquid sample within the predetermined area 40 (first area 41) before the predetermined pressing force is applied to the liquid sample, and can be opened by the liquid sample so that the liquid sample is allowed to flow through the opening into the second area 42 when the predetermined pressing force is applied to the liquid sample.

Figure 3A:
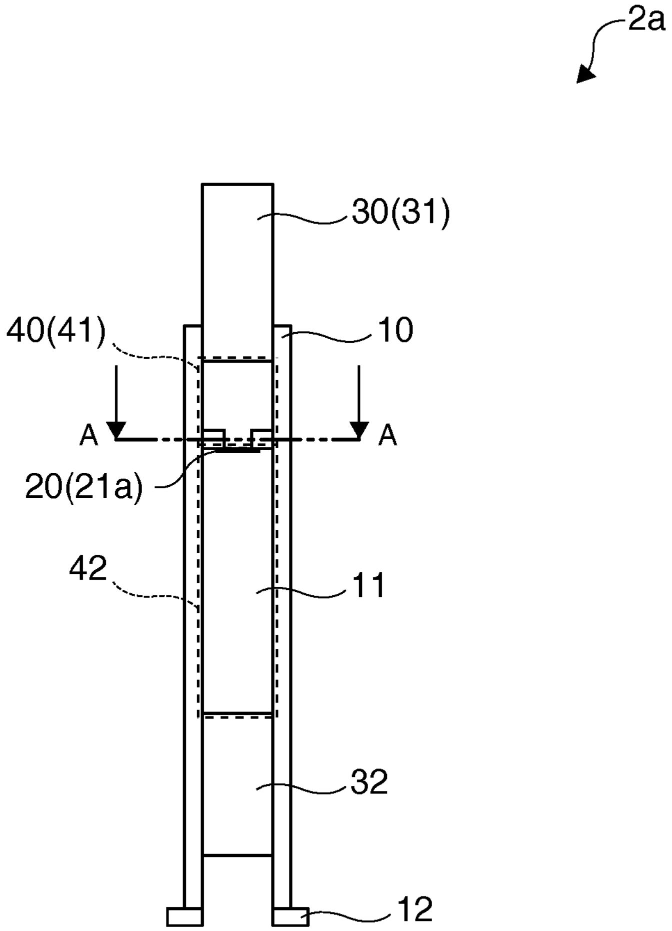
FIG. 3A schematically illustrates a cross-sectional structure of a biochip 2*a* according to a modified example of the second embodiment.
Figure 3B:
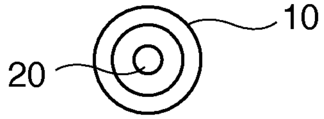
FIG. 3B schematically illustrates a cross section of the biochip 2*a* according to the modified example of the second embodiment taken along a line A-A in FIG. 3A.

FIG. 3A schematically illustrates a cross-sectional structure of a biochip 2*a* according to a modified example of the second embodiment. FIG. 3B schematically illustrates a cross section of the biochip 2*a* according to the modified example of the second embodiment taken along a line A-A in FIG. 3A.

According to the example shown in FIGS. 3A and 3B, the holding unit 20 has a valve 21*a* supported by connection between a support portion 22*a* and a part of a circular plate-shaped component having a circular opening at the center. The plate-shaped component is supported by the close contact between the circumference of the plate-shaped component and the inner surface of the body 10. The valve 21*a* and the support portion 22*a* are disposed on the second area 42 side so as not to excessively limit the shift of the liquid sample from the first area 41 to the second area 42, and are so constructed as to open and close the opening of the plate-shaped component. According to the example shown in FIGS. 3A and 3B, the valve 21*a* functions as a partitioning valve. In case of the example shown in FIGS. 3A and 3B, the valve 21*a* also functions as a non-return valve for allowing the shift of the liquid sample from the first area 41 to the second area 42 and preventing the shift of the liquid sample from the second area 42 to the first area 41.

The size of the opening and the degree of elasticity of the valve 21*a* may be arbitrarily determined as long as the liquid sample can be retained within the predetermined area 40 (first area 41) before the predetermined pressing force is applied to the liquid sample, and can open the valve 21*a* to flow through the opening and shift to the second area 42 when the predetermined pressing force is applied to the liquid sample. The shape of the opening is not limited to the circular shape but may be a polygonal shape, for example. The biochip 2*a* may have a plurality of the openings and the valves 21*a* in correspondence with the openings.

According to these examples, the holding unit 20 has the valve 21 or the valve 21*a*. Therefore, each of the biochips 2 and 2*a* thus constructed becomes a biochip having a simple structure and capable of executing a series of tests using PCR rapidly and efficiently by using the thermal cycler of the type reciprocating a liquid sample within liquid.

The biochip 2 in the second embodiment and the biochip 2*a* in the modified example of the second embodiment have structure similar to that of the biochip 1 in the first embodiment except for the holding unit 20. Thus, advantages similar to those of the biochip 1 in the first embodiment can be offered by the biochips 2 and 2*a*. In addition, modifications similar to those of the biochip 1 can be made.

3. Biochip in Third Embodiment

Figure 4A:
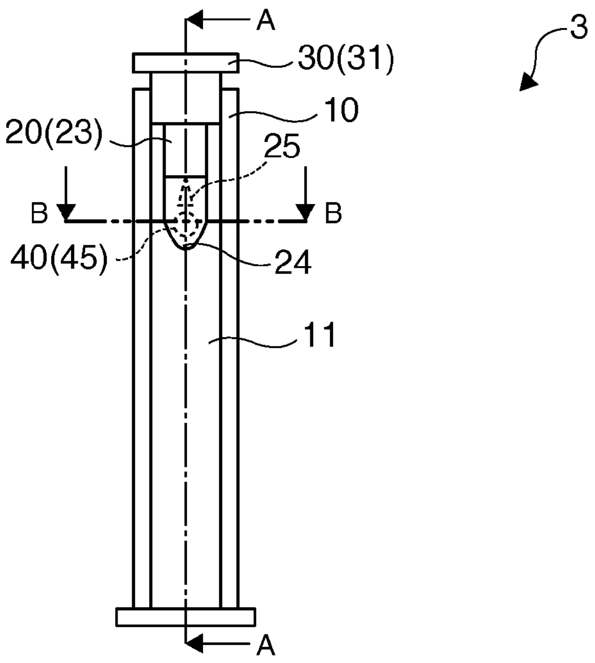
FIG. 4A schematically illustrates a cross-sectional structure of a biochip 3 according to a third embodiment.
Figure 4B:
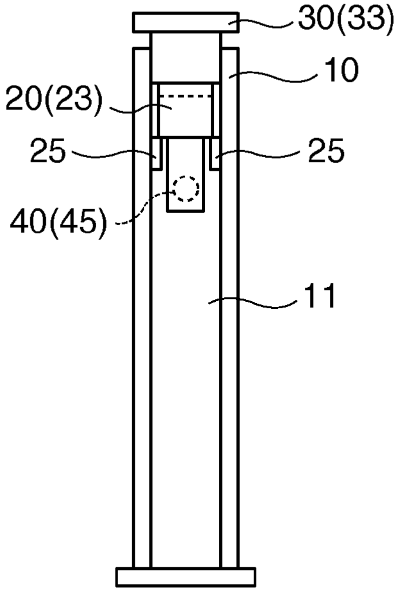
FIG. 4B schematically illustrates a cross section of the biochip 3 according to the third embodiment taken along a line A-A in FIG. 4A.
Figure 4C:
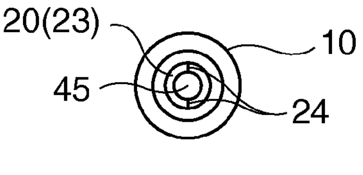
FIG. 4C schematically illustrates a cross section of the biochip 3 according to the third embodiment taken along a line B-B in FIG. 4A.

FIG. 4A schematically illustrates a cross-sectional structure of a biochip 3 in a third embodiment. FIG. 4B schematically illustrates a cross section of the biochip 3 in the third embodiment taken along a line A-A in FIG. 4A. FIG. 4C illustrates a cross section of the biochip 3 in the third embodiment taken along a line B-B in FIG. 4A.

The biochip 3 according to the third embodiment has structure similar to that of the biochip 1 in the first embodiment except for the constructions of the holding unit 20 and the pressed member 30. Thus, similar reference numbers are given to the parts similar to the corresponding parts in the biochip 1 in the first embodiment, and the structures of the holding unit 20 and the pressed member 30 of the biochip 3 are chiefly discussed in the following description.

According to the biochip 3 in the third embodiment, the pressed member 30 applies a predetermined pressing force to the liquid sample via the holding unit 20. Then, the holding unit 20 releases the liquid sample and switches between the liquid sample contained in the predetermined area 40 and oil charged in the chamber 11.

According to the example of the biochip 3 shown in FIGS. 4A and 4B, the pressed member 30 is provided as the movable stopper 33. The movable stopper 33 (pressed member 30) may be formed integrally with the holding unit 20. In case of the example of the biochip 3 shown in FIGS. 4A and 4B, the movable stopper 33 (pressed member 30) can apply the predetermined pressing force to the liquid sample via the holding unit 20.

According to the example of the biochip 3 shown in FIGS. 4A and 4B, the holding unit 20 is provided as an encompassing member 23. The encompassing member 23 has a slit 24 extending from a position away from the movable stopper 33 (pressed member 30) to a position close to the movable stopper 33 (from a lower position to an upper position in FIGS. 4A and 4B) in the direction parallel with the longitudinal direction of the chamber 11. As illustrated in FIGS. 4A through 4C, a cavity 45 forming the predetermined area 40 is provided within the slit 24 of the encompassing member 23. Thus, the cavity 45 is so formed as to communicate with the chamber 11 via the slit 24.

According to the example of the biochip 3 shown in FIGS. 4A and 4B, a wedge 25 is provided on the inner surface of the body 10. The wedge 25 is shaped such that the width decreases from a position away from the movable stopper 33 (pressed member 30) toward a position close to the movable stopper 33 (from a lower position to an upper position in FIGS. 4A and 4B). The wedge 25 is disposed in such a position as to be inserted into the slit 24 when the encompassing member 23 reaches a predetermined position. According to the example shown in FIGS. 4A and 4B, the encompassing member 23 has a wide portion in the surface direction of the slit 24. This structure allows the wedge 25 to be inserted into the slit 24 when the end of the wedge 25 reaches the wide portion.

According to the biochip 3 shown in FIGS. 4A and 4B, the liquid sample can be retained within the cavity 45 (predetermined area 40) of the encompassing member 23. When the predetermined pressing force is applied to the liquid sample via the encompassing member 23 (holding unit 20) by using the movable stopper 33 (pressed member 30), the encompassing member 23 to which the pressing force is applied as well shifts in the direction opposite to the direction toward the movable stopper 33 (downward direction in FIGS. 4A and 4B). As a result, the wedge 25 is inserted into the slit 24 to open the encompassing member 23 and release the liquid sample from the cavity 45 (predetermined area 40). When the chamber 11 is charged with oil, the opened encompassing member 23 can switch between the liquid sample within the cavity 45 (predetermined area 40) and the oil.

Accordingly, the pressed member 30 applies the predetermined pressing force to the liquid sample via the holding unit 20. Then, the holding unit 20 releases the liquid sample and switches between the liquid sample contained within the predetermined area 40 and oil when the chamber 11 is filled with the oil. Thus, variations in the volume of the chamber 11 produced by applying the predetermined pressing force can be reduced.

The structure of the biochip 3 according to the third embodiment other than the holding unit 20 and the pressed member 30 is substantially similar to the structure of the biochip 1 in the first embodiment. Thus, advantages similar to those of the biochip 1 in the first embodiment can be offered by the biochip 3. Moreover, modifications similar to those of the biochip 1 in the first embodiment can be made.

4. Reactor

Figure 5A:
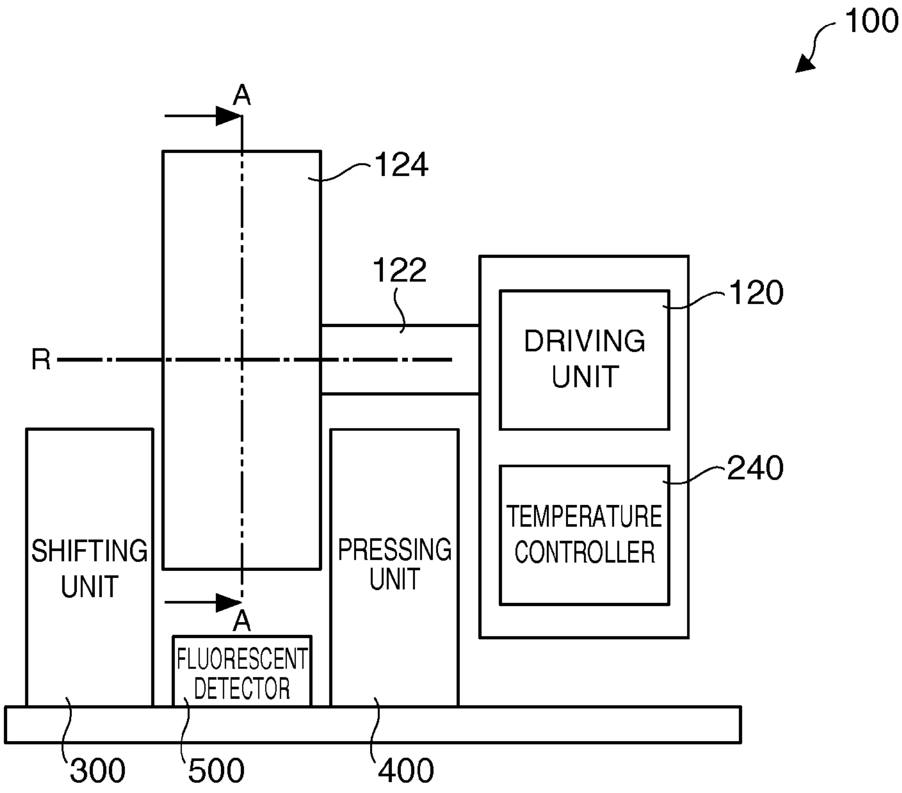
FIG. 5A schematically illustrates a reactor 100 according to an example.
Figure 5B:
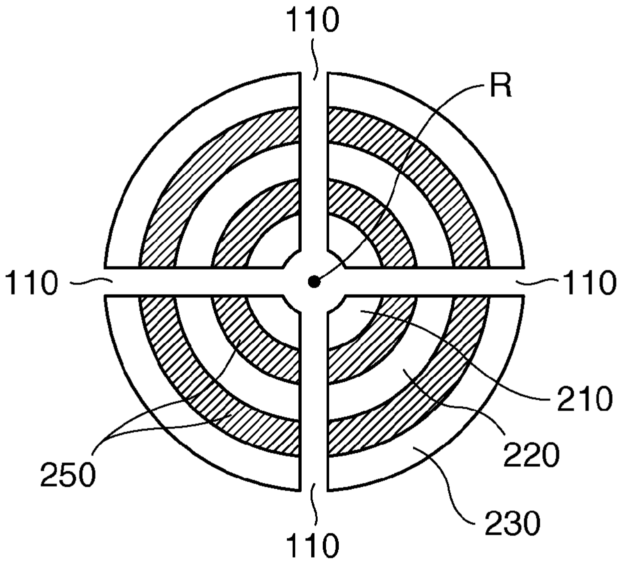
FIG. 5B schematically illustrates a cross section of the reactor 100 according to the example taken along a line A-A in FIG. 5A.

FIG. 5A schematically illustrates a reactor 100 according to an example. FIG. 5B schematically illustrates a cross section of the reactor 100 according to this example taken along a line A-A in FIG. 5A.

The reactor 100 in this example includes a holder 110 for holding a biochip. The biochip held by the holder 110 includes the chamber 11 which has the longitudinal direction, the holding unit 20 which holds a liquid sample within the predetermined area 40 of the chamber 11 provided along the longitudinal direction and releases the liquid sample from the predetermined area 40 to an area within the chamber 11 by using a predetermined pressing force, and the pressed member 30 which applies the predetermined pressing force to the liquid sample. Examples of the biochip used herein involve the biochip 1 according to the first embodiment, the biochip 2 according to the second embodiment, and the biochip 3 according to the third embodiment.

According to the example shown in FIGS. 5A and 5B, the reactor 100 has a cylindrical rotor 124. Each of holders 110 has an opening on the side surface of the rotor 124 as an insertion hole through which the biochip is inserted. Each of the holders 110 may be so constructed as to prevent movement of the biochip by utilizing friction produced between the holder 110 and the outer surface of the held biochip.

The reactor 100 in this example includes a driving unit 120 for rotating the holders 110 around a rotation axis R extending in a direction having a horizontal component. The direction having the horizontal component herein corresponds to a direction having a horizontal vector component, that is, a non-gravity direction. According to the example shown in FIG. 5A, the rotation axis R is a rotation axis extending in the horizontal direction.

According to the example shown in FIGS. 5A and 5B, the driving unit 120 is so constructed as to rotate the holders 110 around the rotation axis R by rotating the rotor 124 around the rotation axis R via a rotation support member 122.

The reactor 100 in this example includes a first heat block disposed within a first distance range from the rotation axis R and controlled to have a first temperature, and a second heat block disposed within a second distance range from the rotation axis R as a range different from the first distance range and controlled to have a second temperature different from the first temperature, both of which heat blocks are so provided as to produce axis-symmetric temperature distribution with respect to the rotation axis R when the biochip is held in the holder 110.

According to the example shown in FIGS. 5A and 5B, a heat block 210, a heat block 220, and a heat block 230 are equipped on the rotor 124 in this order from the position of the rotation axis R. Two heat blocks arbitrarily selected from the heat block 210, the heat block 220, and the heat block 230 correspond to the first heat block and the second heat block.

The heat blocks are controlled by a temperature controller 240 to be heated or cooled to a desired temperature. For example, when the reactor 100 is employed for PCR which performs hot start by using Taq-polymerase after reverse transcription from RNA to cDNA for an RNA virus test such as an influenza virus, the temperatures of the heat block 210, the heat block 220, and the heat block 230 may be adjusted to 45° C., 95° C., and 65° C., respectively. A heat insulator 250 may be provided between each of the adjoining pair of the heat block 210 and the heat block 220 and the adjoining pair of the heat block 220 and the heat block 230 as illustrated in FIG. 5B.

Figure 6:
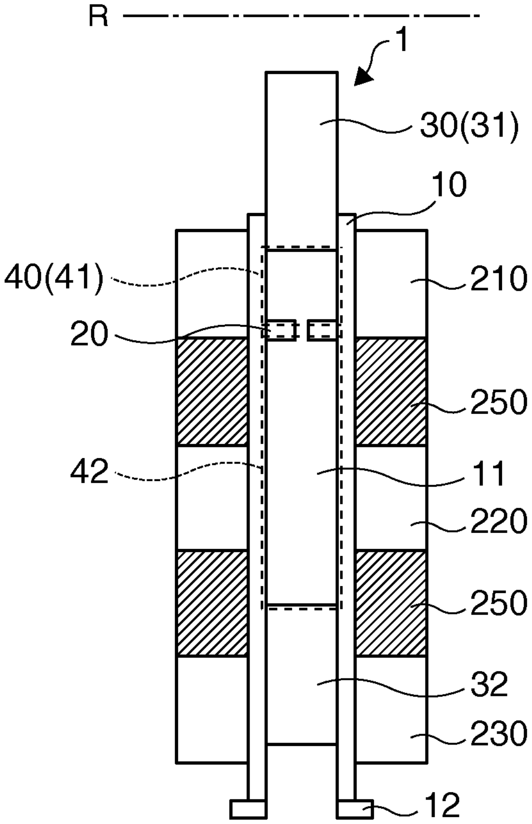
FIG. 6 schematically illustrates a condition in which the biochip 1 is held in a holder 110 of the reactor 100 according to the example.

FIG. 6 schematically illustrates the condition in which the biochip 1 is held in the holder 110 of the reactor 100 according to this example.

According to the reactor 100 in this example, the holder 110 is constructed such that the distance between the rotation axis R and one end of the chamber 11 in the longitudinal direction is different from the distance between the rotation axis R and the other end of the chamber 11, and that at least apart of the predetermined area 40 lies within either the first distance range or the second distance range.

According to the example shown in FIG. 6, the heat block 210 disposed closest to the rotation axis R corresponds to the first heat block, and the distance range of the heat block 210 extending from the rotation axis R corresponds to the first distance range. The holder 110 is constructed such that the predetermined area 40 (first area 41) of the biochip 1 lies within the first distance range extending from the rotation axis R.

According to the example shown in FIG. 6, the heat block 220 disposed second closest to the rotation axis R corresponds to the second heat block, and the distance range of the heat block 220 extending from the rotation axis R corresponds to the second distance range. The holder 110 is constructed such that at least a part of the second area 42 of the biochip 1 lies within the second distance range extending from the rotation axis R.

According to the example shown in FIG. 6, the liquid sample can be maintained at 45° C. equivalent to the temperature of the heat block 210 under the condition of retaining the liquid sample within the predetermined area 40. On the other hand, under the condition of allowing the liquid sample to shift to the outside of the predetermined area 40 (under the condition in which the liquid sample exists in the second area 42) according to the case shown in FIG. 6, the liquid sample can shift within the range of the second area 42 in the longitudinal direction. Thus, the liquid sample can be brought into the temperature cycle corresponding to the temperature distribution in the second area 42 in the longitudinal direction.

Accordingly, in case of the reactor 110 in this example, at least a part of the predetermined area 40 is disposed within the distance of either the first distance range or the second distance range extending from the rotation axis R. Thus, the liquid sample can be maintained in a predetermined temperature condition under the condition of retaining the liquid sample within the predetermined area 40. On the other hand, under the condition of allowing the liquid sample to shift to the outside of the predetermined area 40, the liquid sample can be brought into the predetermined temperature cycle. Therefore, the reactor 110 can perform a series of tests using PCR rapidly and efficiently.

As illustrated in FIG. 5A, the reactor 100 in this example may include a shifting unit 300 which shifts the biochip held in the holder 110. Moreover, as illustrated in FIG. 5A, the reactor 100 in this example may include a pressing unit 400 which applies a predetermined pressing force to the pressed member 30 of the biochip held in the holder 110.

Figure 7:
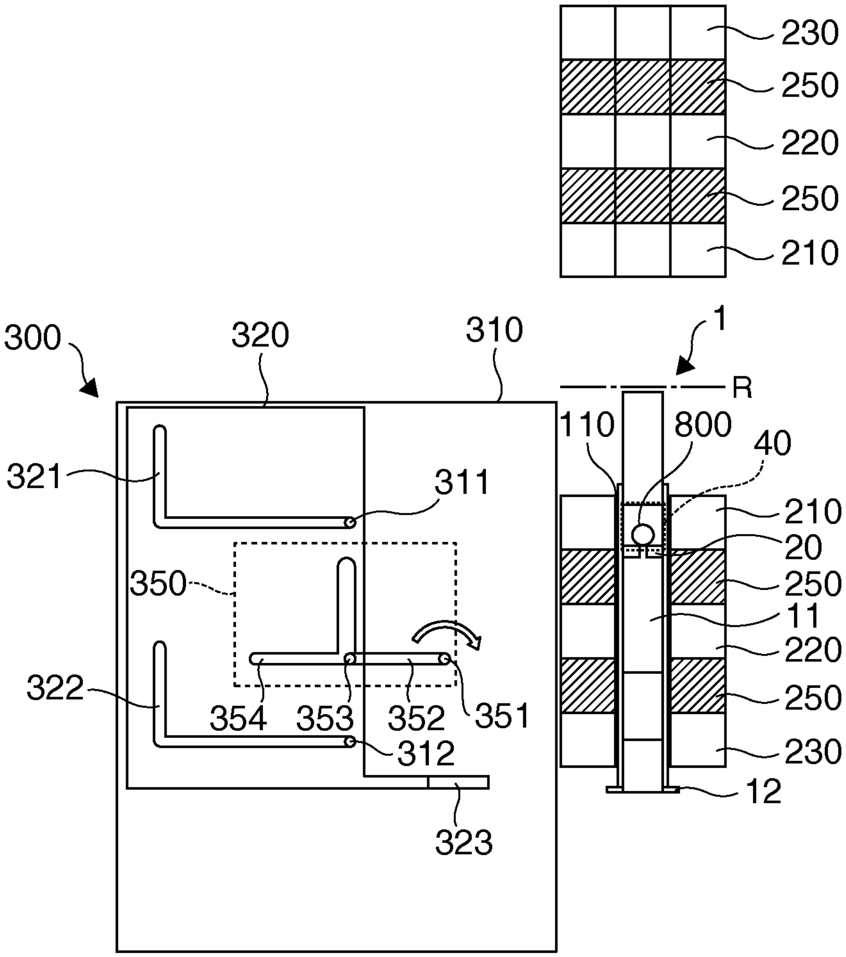
FIG. 7 illustrates an example of a shifting unit 300.
Figure 8:
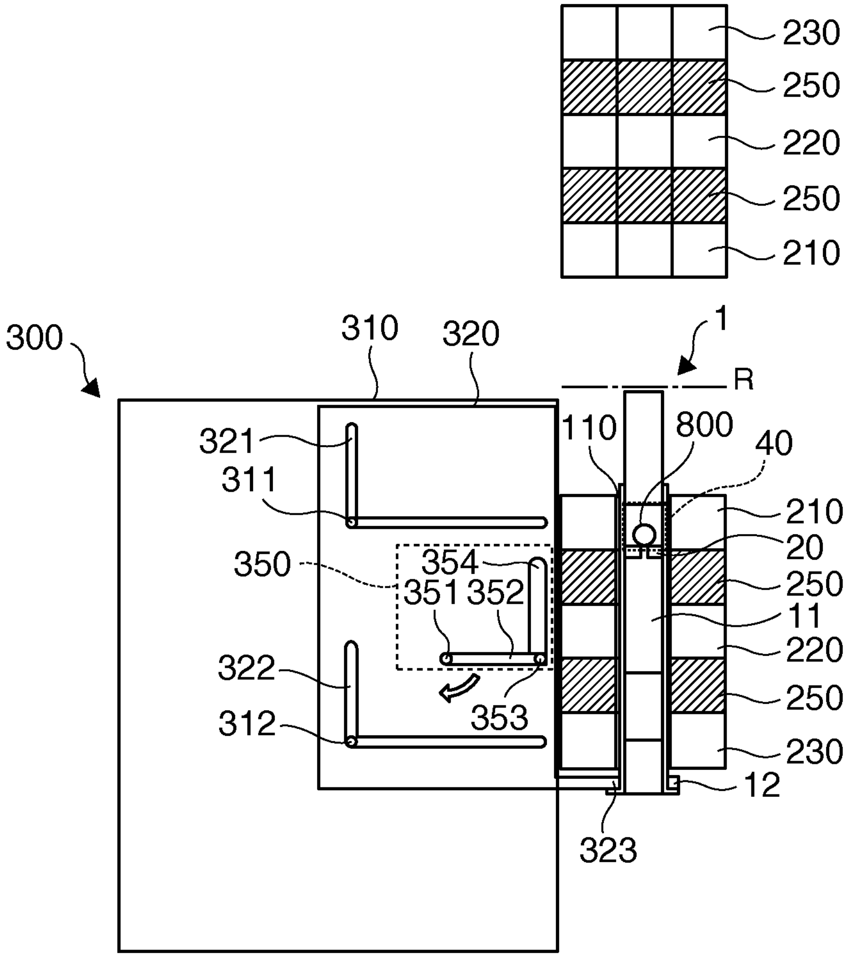
FIG. 8 illustrates the example of the shifting unit 300.
Figure 9:
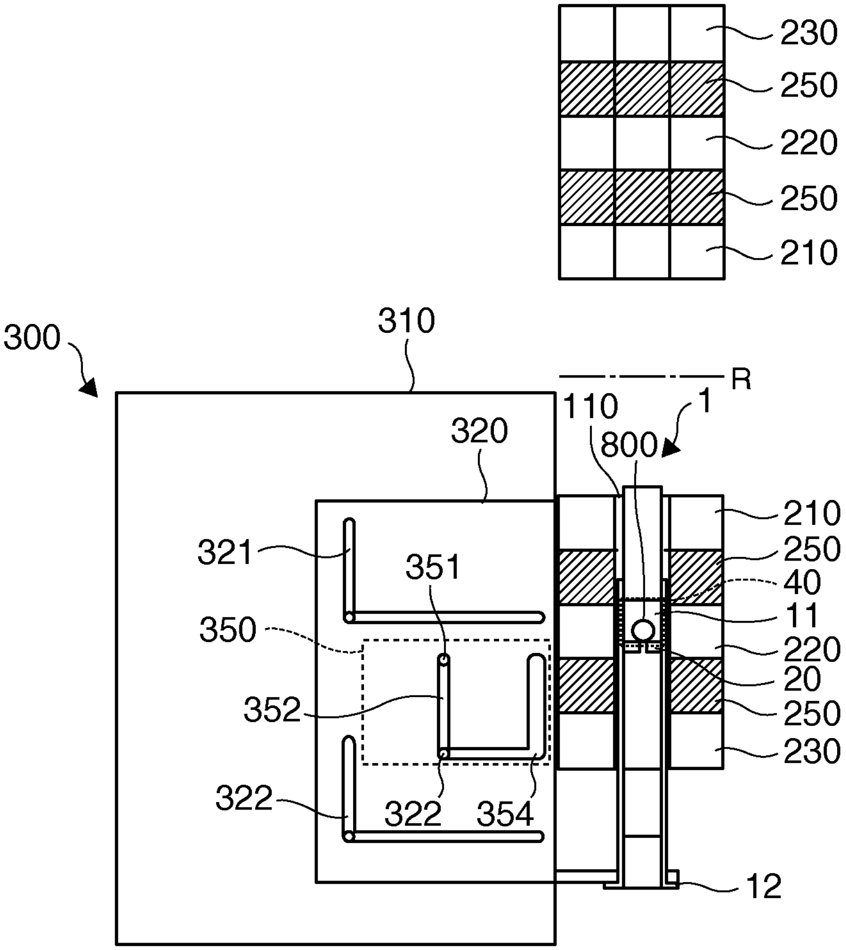
FIG. 9 illustrates the example of the shifting unit 300.

FIGS. 7 through 9 illustrate an example of the shifting unit 300. FIGS. 7 through 9 show the case in which the biochip 1 is held in the holder 110. The chamber 11 of the biochip 1 is filled with oil. A liquid sample 800 as droplets is placed within the predetermined area 40.

According to the example shown in FIG. 7, the shifting unit 300 includes a housing 310 and a movable plate 320. The movable plate 320 has a fork 323 which engages with the fringe 12 of the biochip 1 to apply a downward force to the fringe 12 of the biochip 1.

According to the example shown in FIG. 7, a guide pin 311 and a guide pin 312 are fixed to the housing 310. A guide groove 321 and a guide groove 322 engaging with the guide pin 311 and the guide pin 312, respectively, are formed on the movable plate 320 so that the movable plate 320 can shift with respect to the housing 310 within the shift range of the guide pins 311 and 312 defined by the shapes of the guide grooves 321 and 322. According to the example shown in FIG. 7, each of the guide grooves 321 and 322 is L-shaped so that the movable plate 320 can approach the biochip 1 held in the holder 110 in the horizontal direction and descend in the vertical direction.

According to the example shown in FIG. 7, the shifting unit 300 includes a grooved cam 350. The grooved cam 350 has a driving shaft 351 provided on the housing 310, an arm 352 whose one end is fixed to the driving shaft 351 to rotate around the driving shaft 351 as the rotation axis, a pin 353 disposed at the other end of the arm 352, and an L-shaped cam groove 354 formed on the movable plate 320 and engaging with the pin 353.

The operation of the shifting unit 300 is now explained with reference to FIGS. 7 through 9. When the arm 352 of the grooved cam 350 is rotated clockwise (in the direction of a white arrow in FIG. 7) by the driving shaft 351 through 180 degrees from the position shown in FIG. 7, the movable plate 320 approaches the biochip 1 held in the holder 110 in the horizontal direction. As a result, the fork 323 engages with the fringe 12 of the biochip 1 in the condition shown in FIG. 8.

When the arm 352 of the grooved cam 350 is rotated clockwise (in the direction of a white arrow in FIG. 8) by the driving shaft 351 through 90 degrees from the position shown in FIG. 8, the movable plate 320 descends in the vertical direction to come into a condition shown in FIG. 9 where the biochip 1 is lowered by a downward force applied to the fringe 12 of the biochip 1 via the fork 323.

According to the example shown in FIGS. 7 through 9, the biochip 1 can be shifted from the position corresponding to the heat block 210 to the position corresponding to the heat block 220 while placing the liquid sample 800 within the predetermined area 40.

In this case, the biochip 1 held in the holder 110 can be moved within the range of the holder 110 by using the shifting unit 300. Accordingly, the liquid sample 800 can be shifted to any positions corresponding to the heat blocks having different temperatures.

Figure 10:
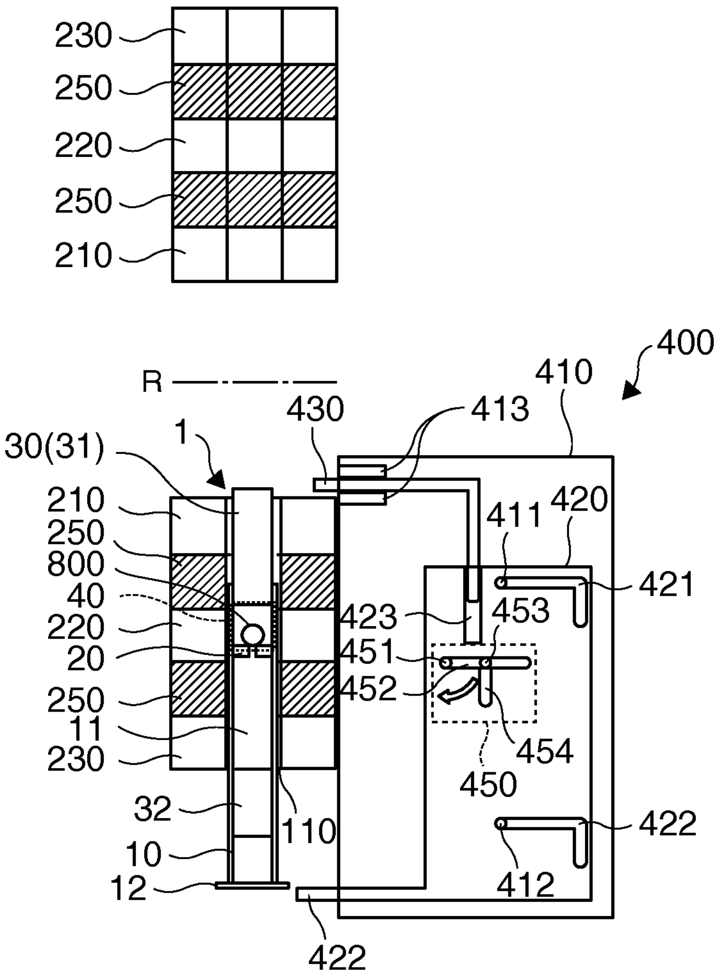
FIG. 10 illustrates an example of a pressing unit 400.
Figure 11:
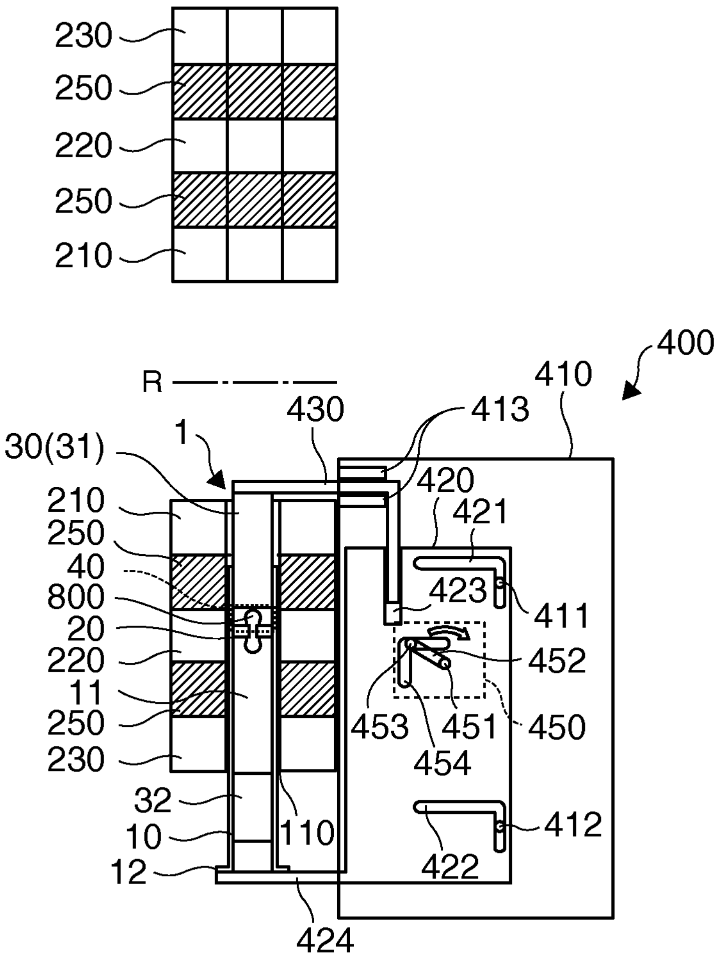
FIG. 11 illustrates the example of the pressing unit 400.
Figure 12:
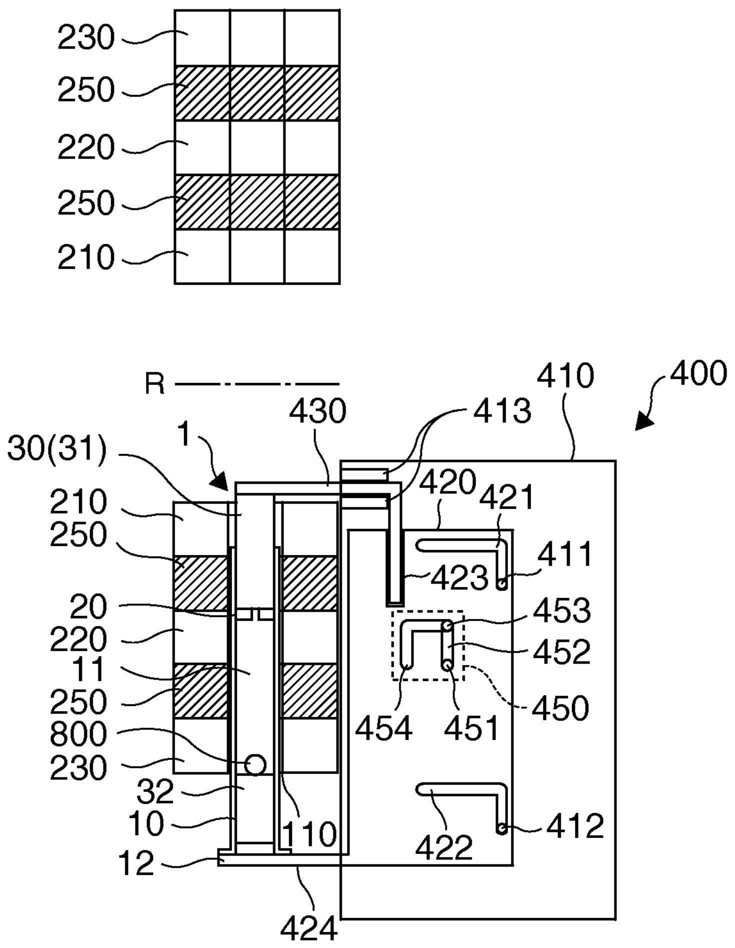
FIG. 12 illustrates the example of the pressing unit 400.

FIGS. 10 through 12 illustrate an example of the pressing unit 400. FIGS. 10 through 12 show the case in which the biochip 1 is held in the holder 110. The chamber 11 of the biochip 1 is filled with oil. The liquid sample 800 is placed as droplets within the predetermined area 40.

According to the example shown in FIG. 10, the pressing unit 400 includes a housing 410, a movable plate 420, and a movable stopper pressing plate 430. The movable plate 420 has a fork 424 which engages with the fringe 12 of the biochip 1 to apply an upward force to the fringe 12 of the biochip 1.

According to the example shown in FIG. 10, a guide pin 411 and a guide pin 412 are fixed to the housing 410. A guide groove 421 and a guide groove 422 engaging with the guide pin 411 and the guide pin 412, respectively, are formed on the movable plate 420 so that the movable plate 420 can shift with respect to the housing 410 within the shift range of the guide pins 411 and 412 defined by the shapes of the guide grooves 421 and 422. According to the example shown in FIG. 10, each of the guide grooves 421 and 422 is L-shaped so that the movable plate 420 can approach the biochip 1 held in the holder 110 in the horizontal direction and descend in the vertical direction.

According to the example shown in FIG. 10, the pressing unit 400 includes a grooved cam 450. The grooved cam 450 has a driving shaft 451 provided on the housing 410, an arm 452 whose one end is fixed to the driving shaft 451 to rotate around the driving shaft 451 as the rotation axis, a pin 453 disposed at the other end of the arm 452, and an L-shaped cam groove 454 formed on the movable plate 420 and engaging with the pin 453.

According to the example shown in FIG. 10, a guide plate 413 for limiting the vertical movement of the L-shaped movable stopper pressing plate 430 is provided on the housing 410. A guide groove 423 is formed on the movable plate 420 as a groove which does not allow the movable stopper pressing plate 430 to follow the vertical shift of the movable plate 420 but allows the movable stopper pressing plate 430 to follow the horizontal shift of the movable plate 420.

The operation of the pressing unit 400 is now explained with reference to FIGS. 10 through 12. When the arm 452 of the grooved cam 450 is rotated clockwise (in the direction of a white arrow in FIG. 10) by the driving shaft 451 through 180 degrees from the position shown in FIG. 10, the movable plate 420 approaches the biochip 1 held in the holder 110 in the horizontal direction. As a result, the fork 423 is brought into engagement with the fringe 12 of the biochip 1, allowing the movable stopper pressing plate 430 to shift to the condition of pressing the upper part of the movable stopper 31. In other words, the biochip 1 comes into a condition sandwiched between the fork 424 and the movable stopper pressing plate 430.

When the arm 452 of the grooved cam 450 is rotated clockwise (in the direction of a white arrow in FIG. 11) by the driving shaft 451 as illustrated in FIG. 11, the movable plate 420 rises in the vertical direction with the position of the movable stopper pressing plate 430 unchanged. Then, the body 10 of the biochip 1 is pushed up by an upward force applied to the fringe 12 of the biochip 1 via the fork 423. When the arm 452 of the grooved cam 450 is rotated clockwise (in the direction of the white arrow shown in FIG. 11) by the driving shaft 451, the condition shown in FIG. 12 is produced. Accordingly, the liquid sample 800 can be released from the predetermined area 40 (first area 41) by applying the predetermined pressing force produced by the upward shift of the body 10 to the liquid sample 800 placed within the predetermined area 40 via the movable stopper 31 (pressed member 30) without changing the position of the movable stopper 31.

According to the example shown in FIGS. 10 through 12, the pressing force can be applied to the liquid sample 800 via the movable stopper 31 (pressed member 30) without changing the position of the oil charged into the chamber 11 with respect to the heat block. Thus, the liquid sample 800 can be brought into the temperature cycle in a stable condition of the temperature distribution of the oil charged into the chamber 11.

Accordingly, the predetermined pressing force can be applied to the liquid sample 800 placed within the predetermined area 40 via the movable stopper 31 (pressed member 30) by using the pressing unit 400.

As illustrated in FIG. 5A, the reactor 100 in this example may include a fluorescent detector 500. According to the example shown in FIG. 5A, the fluorescent detector 500 is disposed below the rotor 124. Examples of the fluorescent detector 500 involve an area sensor, a line sensor, and a point sensor using a CCD (charge coupled device) image sensor or a CMOS (complementary metal oxide semiconductor) image sensor.

According to this structure, fluorescence detection can be executed with the biochip inserted in the holder 110 of the reactor 100. Thus, the reactor 100 becomes a device suited for real-time PCR measurement.

5. Reaction Method

Figure 13:
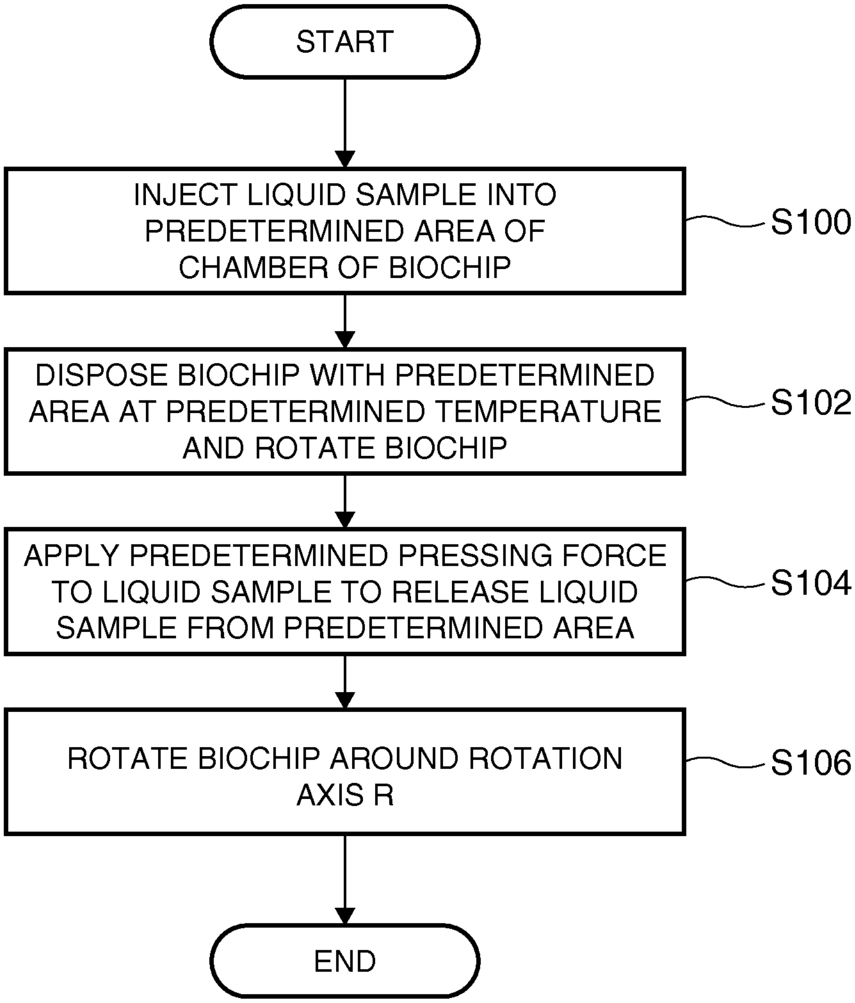
FIG. 13 is a flowchart showing a reaction method according to an example.

FIG. 13 is a flowchart showing a reaction method according to an example.

The reaction method according to this example includes an injection step for injecting a liquid sample into a predetermined area of a chamber of a biochip which contains a chamber having a longitudinal direction, a holding unit holding the liquid sample within a predetermined area of the chamber provided along the longitudinal direction and releasing the liquid sample from the predetermined area to an area within the chamber by using a predetermined pressing force, and a pressed member applying the predetermined pressing force to the liquid sample (step S100), a first rotation step which disposes the predetermined area in such a condition that the predetermined area has a predetermined temperature while retaining the liquid sample within the predetermined area by using the holding unit, and rotates the biochip around the rotation axis R located in such a position that the distance between the rotation axis and one end of the chamber in the longitudinal direction is different from the distance between the rotation axis and the other end of the chamber and having a horizontal component (step S102), a pressing step which applies the predetermined pressing force to the liquid sample by using the pressed member to release the liquid sample from the predetermined area to an area within the chamber (step S104), and a second rotation step which rotates the biochip around the rotation axis R (step S106).

Examples of the biochip used in the reaction method in this example involve the biochip 1 according to the first embodiment, the biochip 2 according to the second embodiment, and the biochip 3 according to the third embodiment.

FIGS. 14A through 14D schematically illustrate steps of the reaction method according to this example using the biochip 1 and the reactor 100. The chamber 11 of the biochip 1 is filled with oil not miscible with the liquid sample 800. The liquid sample 800 contains an enzyme or the like necessary for reaction as well as a sample.

Initially, the injection step for injecting the liquid sample 800 into the predetermined area 40 of the chamber 11 of the biochip 1 is performed (step S100).

Then, the first rotation step which disposes the predetermined area 40 in such a condition that the predetermined area 40 has a predetermined temperature while retaining the liquid sample 800 within the predetermined area 40 by using the holding unit 20, and rotates the biochip 1 around the rotation axis R located in such a position that the distance between the rotation axis and one end of the chamber in the longitudinal direction is different from the distance between the rotation axis and the other end of the chamber and having a horizontal component (step S102).

Figures 14A, 14B, 14C, 14D:
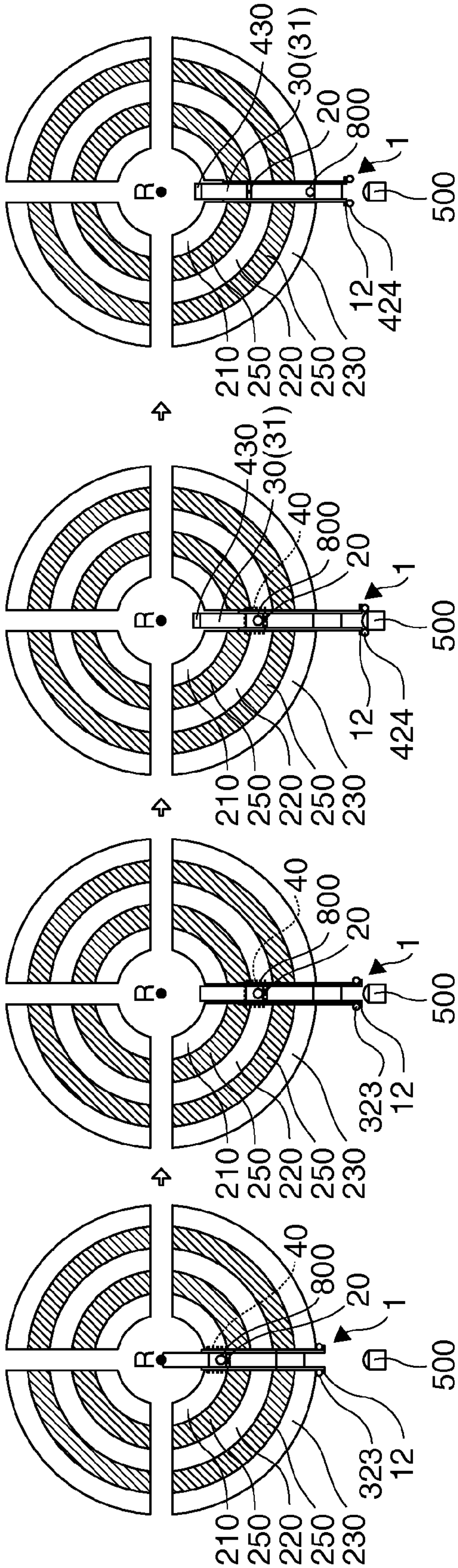
FIGS. 14A through 14D schematically illustrate steps performed by the reaction method according to the example using the biochip 1 and the reactor 100.

According to the example shown in FIG. 14A, the predetermined area 40 is disposed at a position corresponding to the heat block 210 controlled to have 45° C. so that the temperature of the predetermined area 40 becomes 45° C. When the biochip 1 is rotated around the rotation axis R under the condition shown in FIG. 14A, the liquid sample 800 remaining within the predetermined area 40 is kept placed within the predetermined area 40 adjusted to 45° C. regardless of the rotation of the biochip 1. In case of cDNA after reverse transcription of RNA, for example, the biochip 1 may be rotated for about 30 minutes under the condition shown in FIG. 14A.

According to the example shown in FIG. 14B, the predetermined area 40 is disposed at a position corresponding to the heat block 220 controlled to have 95° C. so that the temperature of the predetermined area 40 becomes 95° C. The condition shown in FIG. 14A may be switched to the condition shown in FIG. 14B by applying a downward force to the fringe 12 of the biochip 1 via the fork 323 of the shifting unit 300 illustrated in FIGS. 7 through 9, for example. When the biochip 1 is rotated around the rotation axis R under the condition shown in FIG. 14B, the liquid sample 800 remaining within the predetermined area 40 is kept placed in the predetermined area 40 adjusted to 95° C. regardless of the rotation of the biochip 1. In case of PCR performing hot start by using Taq polymerase, for example, the biochip 1 may be rotated for about 5 minutes under the condition shown in FIG. 14B.

Next, the pressing step which applies the predetermined pressing force to the liquid sample 800 by using the pressed member 30 to release the liquid sample 800 from the predetermined area 40 to an area within the chamber 11 (step S104). For example, the predetermined pressing force may be applied to the liquid sample 800 by applying a force such that the fringe 12 of the biochip 1 and the movable stopper 31 (pressed member 30) can be sandwiched between the fork 424 of the pressing unit 400 and the movable stopper pressing plate 430 as illustrated in FIGS. 10 through 12. By this method, the condition shown in FIG. 14C in which the liquid sample 800 is retained within the predetermined area 40 can be switched to the condition shown in FIG. 14D in which the liquid sample 800 is released from the predetermined area 40 to an area within the chamber 11.

Then, the biochip 1 is rotated around the rotation axis R (step S106). When the biochip 1 is rotated around the rotation shaft R under the condition shown in FIG. 14D, the biochip 1 revolves in such a condition that the distance between the lowermost position within the chamber 11 in the direction of gravity and the rotation axis R varies under the condition in which the liquid sample 800 is released from the predetermined area 40 to an area within the chamber 11. Thus, unlike the condition in which the liquid sample 800 remains within the predetermined area 40, the liquid sample 800 shifts within the chamber 11 to be brought into the temperature cycle based on the temperature distribution of the chamber 11 in the longitudinal direction. For example, when DNA is amplified by shuttle PCR, the biochip 1 may be disposed in such a position as to cross over the position corresponding to the heat block 220 adjusted to 95° C. and the position corresponding to the heat block 230 adjusted to 63° C. and may be rotated around the rotation axis Rat a rotation speed of about 15 seconds per one rotation. By this method, the liquid sample 800 can be brought into the temperature cycle changing between 95° C. and 63° C. Moreover, real-time PCR measurement can be achieved by executing fluorescent detection for each rotation using the fluorescent detector 500.

According to the reaction method in this example, the condition of retaining the liquid sample 800 within the predetermined area 40 and the condition of allowing the liquid sample 800 to shift to the outside of the predetermined area 40 can be switched by using the predetermined pressing force based on the pressing step which applies the predetermined pressing force to the liquid sample 800 by the function of the pressed member 30 to release the liquid sample 800 from the predetermined area 40 to an area within the chamber 11 (step S104). In this case, the liquid sample 800 can be maintained in the predetermined temperature state under the condition of retaining the liquid sample 800 within the predetermined area 40, and can be brought into the predetermined temperature cycle under the condition of allowing the liquid sample 800 to shift to the outside of the predetermined area 40. Accordingly, the reaction method can perform a series of tests using PCR smoothly and efficiently.

The invention is not limited to the embodiments and modified examples described and depicted as only examples herein. For example, a plurality of the respective embodiments and modified examples may be combined in appropriate manners.

Therefore, various modifications are included in the scope of the invention. For example, structure substantially similar to the corresponding structure described in the respective embodiments and examples (such as structure including similar functions, methods and results, or structure for similar purposes and advantages) is included in the scope of the invention. Moreover, structure described in the respective embodiments and examples and containing parts which are not essential and are replaced with other parts is included in the scope of the invention. Furthermore, structure providing advantages similar to those of the structure described in the respective embodiments and examples is included in the scope of the invention. In addition, structure described in the respective embodiments and examples to which known techniques are added is included in the scope of the invention.

What is claimed is:

1. A reactor comprising:

a biochip, the biochip including:

a chamber having a longitudinal direction, the chamber including a first area and a second area;

a holding unit having a valve that separates the first and second areas, the holding unit holding a liquid sample within the first area, and releasing the liquid sample from the first area to the second area by a predetermined pressing force;

a pressed member operable to apply the predetermined pressing force to the liquid sample;

a first movable stopper that seals one end of the chamber in the longitudinal direction positioned near the first area; and a second movable stopper that seals another end of the chamber in the longitudinal direction, the second movable stopper being disposed within the chamber, wherein the pressed member comprises the first movable stopper;

and the holding unit is arranged between the first movable stopper and the second movable stopper in the longitudinal direction;

a cylindrical holder that includes a plurality of radially-inwardly-extending apertures for supporting a plurality of the biochips;

a driving unit that rotates the holder around a rotation axis; and a first heat block disposed radially outward a first distance from and encircling the rotation axis and controlled to have a first temperature, and a second heat block disposed radially outward a second distance range from and encircling the first heat block and controlled to have a second temperature different from the first temperature.

2. The biochip according to claim 1, wherein the holding unit reduces a cross-sectional area of the chamber on a plane perpendicular to the longitudinal direction to a cross-sectional area of a predetermined area of the chamber on the plane perpendicular to the longitudinal direction.

3. The biochip according to claim 1, wherein the pressed member applies the predetermined pressing force to the liquid sample via the holding unit; and the holding unit releases the liquid sample from the first area to the second area such that the liquid sample intermixes with an oil present in the second area.

4. The biochip of claim 1, wherein the holding unit consists of a circular-shaped plate having an aperture formed at a center thereof, the aperture being dimensioned to prevent flow of the liquid sample from the first area to the second area in the absence of the predetermined pressing force.

5. The biochip according to claim 1, wherein the holding unit is fixed to the inner surface of the chamber.

6. A reactor comprising:

a cylindrical holder that holds a biochip in a direction orthogonal to a rotational axis of the holder, the biochip including a chamber having a longitudinal direction, a holding unit having a valve that holds a liquid sample within a first area of the chamber provided along the longitudinal direction and releases the liquid sample from the first area to a second area inside the chamber by a predetermined pressing force; a pressed member that applies the predetermined pressing force to the liquid sample; a first movable stopper that seals one end of the chamber in the longitudinal direction positioned near the first area; and a second movable stopper that seals another end of the chamber in the longitudinal direction, the second movable stopper being disposed within the chamber, wherein the pressed member comprises the first movable stopper, and the holding unit is arranged between the first movable stopper and the second movable stopper in the longitudinal direction a driving unit that rotates the holder around the rotation axis having a horizontal component;

a first heat block disposed within a first distance range that is positioned radially outward from and encircles the rotation axis, and is controlled to have a first temperature; and a second heat block disposed within a second distance range that is positioned radially outward from and encircles the rotational axis as a range different from the first distance range, and is controlled to have a second temperature different from the first temperature, wherein the holder is constructed so that the distance between the rotation axis and one end of the chamber in the longitudinal direction is different from the distance between the rotation axis and the other end of the chamber, and that at least a part of the first area lies either within the first distance range from the rotation axis or within the second distance range from the rotation axis, under the condition in which the biochip is held in the holder.

7. The reactor of claim 6, wherein the holding unit consists of a circular-shaped plate having an aperture formed at a center thereof, the aperture being dimensioned to prevent flow of the liquid sample from the first area to the second area in the absence of the predetermined pressing force.

8. A reactor comprising:

a biochip, the biochip including:

a chamber having a longitudinal direction, the chamber including a first area and a second area;

a holding unit consisting of a circular-shaped plate having an aperture formed at a center thereof that separates the first and second areas, the holding unit holding a liquid sample within the first area, and releasing the liquid sample from the first area to the second area by a predetermined pressing force;

a first movable stopper at a first end of the chamber that seals the first end of the chamber and, when depressed, is operable to apply the predetermined pressing force to the liquid sample held within the first area; and a second movable stopper disposed at a second and opposite end of the chamber that seals the second end of the chamber, the second movable stopper being disposed within the chamber, wherein the aperture is dimensioned to prevent flow of the liquid sample from the first area to the second area in the absence of the predetermined pressing force;

and the holding unit is arranged between the first movable stopper and the second movable stopper in the longitudinal direction;

a cylindrical holder that includes a plurality of radially-inwardly-extending apertures for supporting a plurality of the biochips;

a driving unit that rotates the holder around a rotation axis; and a first heat block disposed radially outward a first distance from and encircling the rotation axis and controlled to have a first temperature, and a second heat block disposed radially outward a second distance range from and encircling the first heat block and controlled to have a second temperature different from the first temperature.

* * * * *